United States Patent [19]

Peluso et al.

[11] Patent Number: 4,624,664
[45] Date of Patent: Nov. 25, 1986

[54] ANTIBACTERIAL CLOSURE SYSTEM

[75] Inventors: Francesco Peluso, Louvain; Patrick Balteau, St. Geores sur Meuse, both of Belgium

[73] Assignee: Travenol European Research and Development Centre (TERADEC), Brussels, Belgium

[21] Appl. No.: 838,875

[22] Filed: Mar. 10, 1986

Related U.S. Application Data

[63] Continuation of Ser. No. 757,586, Jul. 22, 1985, abandoned.

[51] Int. Cl.⁴ .................... A61M 25/00; A61M 1/28
[52] U.S. Cl. .................................... 604/256; 604/905
[58] Field of Search ............... 604/29, 256, 280, 283, 604/905

[56] References Cited

U.S. PATENT DOCUMENTS

| 4,346,703 | 8/1982 | Dennehey et al. |
| 4,417,890 | 11/1983 | Dennehey et al. ............... 604/256 |
| 4,431,424 | 2/1984 | Svensson ........................... 604/905 |
| 4,432,764 | 2/1984 | Lopez ............................... 604/905 |
| 4,439,188 | 3/1984 | Dennehey et al. |
| 4,440,207 | 4/1984 | Genatempo et al. ............. 604/256 |
| 4,551,146 | 11/1985 | Rogers ............................. 604/905 |

Primary Examiner—C. Fred Rosenbaum
Assistant Examiner—Michelle N. Lester
Attorney, Agent, or Firm—Paul C. Flattery; Daniel D. Ryan

[57] ABSTRACT

A closure system includes a connector and a protective cap in which there is a liquid antiseptic. As the cap and connector are joined together, multiple seals are formed to trap the liquid antiseptic within the cap and force the antiseptic into the bore of the connector.

6 Claims, 7 Drawing Figures

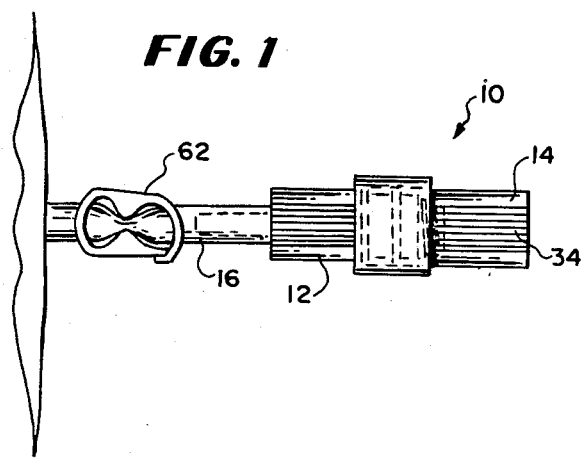
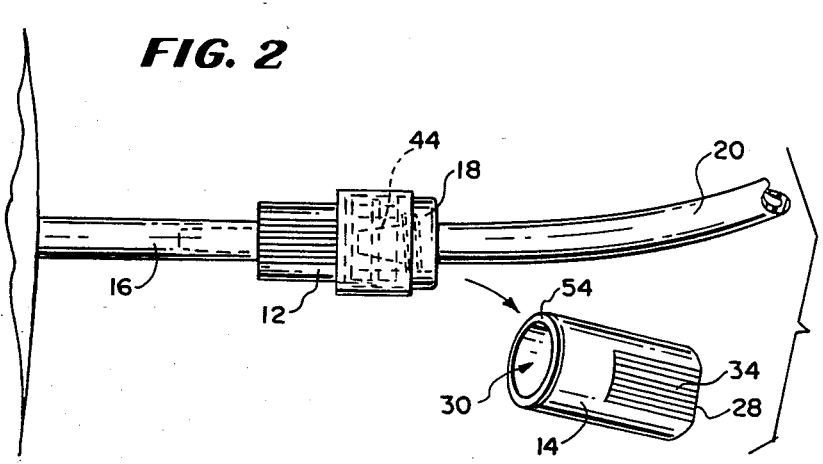
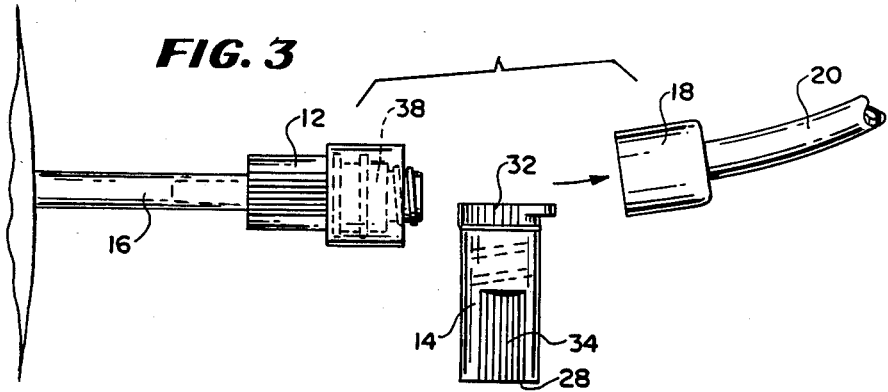

ANTIBACTERIAL CLOSURE SYSTEM

This is a continuation of application Ser. No. 757,586, filed July 22, 1985, now abandaned.

FIELD OF THE INVENTION

This invention relates to closure systems for medical tubing or for ports on medical apparatus. The invention particularly relates to closure systems which provide an antibacterial effect.

BACKGROUND OF THE INVENTION

Medical procedures often require a connection where the bioburden (i.e., bacterial population) is minimized. Closure systems containing an antibacterial agent can reduce the bioburden by providing a bacteriocidal or bacteriostatic effect to the connection site prior to and after use. Closure systems having an antibacterial effect are particularly desirable for components used in peritoneal dialysis.

At the present time thousands of patients who have limited or nonexistent kidney function due to end state renal disease are being maintained by continuous ambulatory peritoneal dialysis (CAPD), along with other forms of peritoneal dialysis.

In the CAPD procedure, connections between dialysis solution containers and administration sets which communicate with the peritoneal catheter must be routinely made and broken, normally several times a day. Particularly when the patient is doing the CAPD exchanges alone, there is the possibility that the sterility of the flow path between the various solution containers and the peritoneal cavity may be compromised. Airborne bacteria or the accidental contamination of an open connector by the patient can contaminate the flow path. The result of such a contamination can be peritonitis.

Closure systems for medical connectors, such as CAPD connectors, have been developed.

For example, in the Quinton Cap manufactured by Quinton Instrument Co., a liquid antiseptic such as povidone iodine, is injected into the lumen of the catheter by means of a syringe and then covered with a cap.

As another example, Lopez U.S. Pat. No. 4,432,764 discloses an antiseptic end cap for a catheter. The end cap has a reservoir, in which a liquid antiseptic is retained. A movable wall can be displaced to force the liquid antiseptic from the reservoir into the bore of the catheter.

As yet another example, Genatempo et al U.S. Pat. No. 4,440,207, which is assigned to the assignee of the present invention, discloses an end cap for a connector which is lined with an absorbent material containing an antiseptic.

BRIEF SUMMARY OF THE INVENTION

The present invention provides a closure system which combines simplicity of operation with an enhanced antibacterial effect.

The closure system which embodies the features of the invention includes a connector and an associated protective cap. The connector includes a luer fitment having an interior bore and a skirt which peripherally surrounds the luer fitment. The cap has an exterior wall surface and an interior wall surface defining an interior chamber. A liquid antiseptic is retained in the interior chamber.

As the cap and connector are joined together, the luer fitment is moved progressively into the antiseptic-filled chamber. A first seal area is formed between the exterior cap wall surface and the skirt surrounding the fitment. In addition, a second seal area is formed between the interior cap wall surface and the luer fitment itself. These dual seal areas trap the liquid antiseptic within the cap cavity. As the advancing luer fitment occupies more and more of the double-sealed cap chamber, the trapped liquid antiseptic is forced into the bore of the luer fitment.

In the preferred embodiment, the luer fitment includes external threads. The cap further includes internal threads which engage the external threads of the luer fitment to provide a secure threaded connection between the connector and cap.

Other features and advantages of the invention will be pointed out in, or will be apparent from, the specification and claims, as will obvious modification of the embodiments shown in the drawings.

BRIEF DESCRIPTION OF THE DRAWINGS

FIG. 1 is a plan view of a closure system which embodies the features of the invention and in which the associated connector and cap are joined together;

FIG. 2 is another view of the closure system shown in FIG. 1 with the cap removed and the connector joined to a second mating connector;

FIG. 3 is another view of the closure system shown in FIG. 2 after the mating connectors have been disconnected and prior to the attachment of a new cap;

Figure 4:
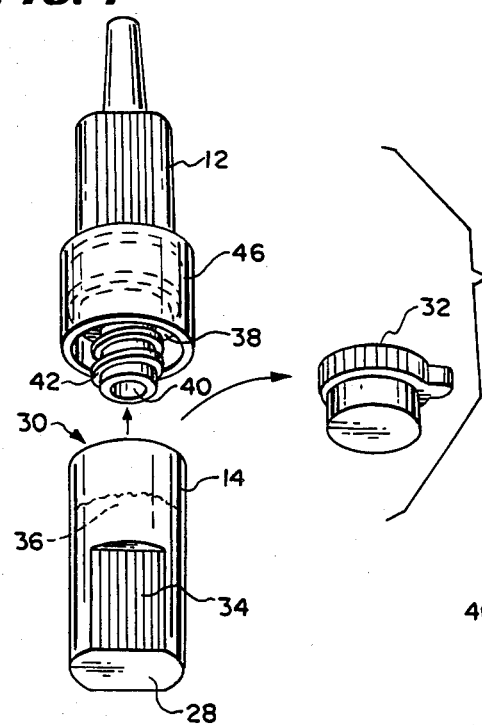
FIG. 4 is an enlarged perspective view of the closure system shown in FIG. 1.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed is for the purpose of description and should not be regarded as limiting.

DESCRIPTION OF THE PREFERRED EMBODIMENTS

A closure system 10 which embodies the features of the invention is shown in FIG. 1. The system 10 includes a luer-type connector 12 and a removable protective cap 14 for the connector 12.

The system 10 can be used in different operative environments. In the illustrated embodiment, the system 10 is used in conjunction with a peritoneal dialysis procedure. In this modality, the connector 12 is carried at the end of a catheter 16 which communicates with the peritoneal cavity of a patient. An extension set (not shown) can be used to interconnect the connector 12 with the end of the catheter 16. The cap 14 not only serves to protect the interior portions of the connector 12 from touch contact, but it also serves to provide an active antibacterial effect to prevent contamination of the connector 12 and adjacent portions of the catheter 16 or extension set. The closure system 10 thus reduces the potential for peritonitis, which is always a matter of paramount concern in peritoneal dialysis.

In use, the protective cap 14 is removed to expose the connector 12, when desired. This is shown in FIG. 2. The connector 12 can then be conveniently attached to suitable mating connector 18. As shown in FIG. 2, the mating connector 18 is carried at the end of a fluid administration set 20.

Once the resulting connection has been made between the connectors 12 and 18, spent peritoneal dialysis solution can be conducted out of the peritoneal cavity of the patient. Fresh peritoneal dialysis solution can then be conducted back into the peritoneal cavity so that the peritoneal dialysis process can continue. Upon the introduction of fresh dialysis solution, the two connectors 12 and 18 are separated, breaking the connection. This is shown in FIG. 3.

A new protective cap 14 is now attached to the connector 12. The protective cap 14 remains on the connector 12 (as shown in FIG. 1) while the just-freshly introduced peritoneal solution dwells within the peritoneal cavity for a predetermined period, typically about six hours. During this dwell period, the patient is free to carry on his or her activities, with the closure system 10 unobtrusively hidden beneath his or her clothing.

At the end of the dwell period, the cap 14 is removed and, preferably, discarded. Another exchange of spent-for-fresh peritoneal solution is made in the manner just described.

Figure 5:
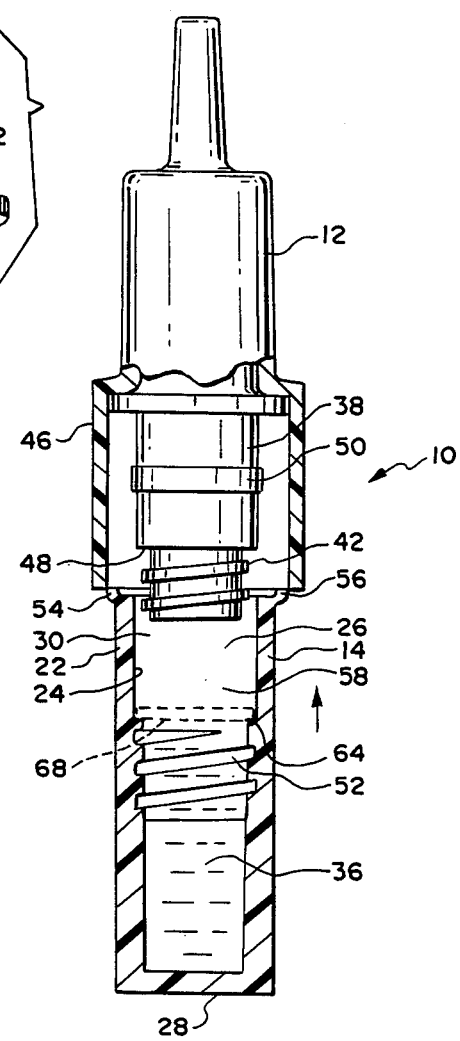
FIGS. 5 to 7 are side views, partly in section, of the closure system as the connector and cap are being progressively brought together.

As best shown in FIGS. 4 and 5, the protective cap 14 comprises a generally cylindrical body having an exterior wall surface 22 and an interior wall surface 24. The interior wall surface 24 defines an interior chamber 26. The chamber 26 has a closed end 28 and an open end 30. As shown in FIG. 3, the open end 30 is sealed prior to use by a removable plug 32.

The exterior wall surface 22 of the cap 14 may include a flattened, roughened portion 34 to facilitate the patient's grip on the cap 14 during its attachment and removal from the connector 12.

A liquid antiseptic 36 is carried within the cap chamber 26 to provide an active bacteriocidal effect when the cap 14 is attached to the connector 12. Prior to use, the plug 32 retains the antiseptic 36 within the chamber 26.

As is also best shown in FIGS. 4 and 5, the connector 12 includes a luer fitment 38 and an annular skirt 46 which peripherally surrounds the fitment 38. While the luer fitment 38 may vary, in the illustrated embodiment, the fitment 38 comprises a female luer having a standard tapered interior bore 40. In the illustrated embodiment, the fitment 38 also includes a threaded distal end 42.

In this arrangement, the mating connector 18 comprises a suitably threaded male luer fitment 44 (shown in phantom lines in FIG. 1) which threadably engages the threaded distal end 42 within the skirt 46 and which sealingly occupies the bore 40 of the female luer fitment 38.

As best shown in FIG. 5, the threaded distal end 42 of the luer fitment 38 has an outer diameter which is less than the outer diameter of the rest of the fitment 38. An annular shoulder 48 is thus created on the fitment 38 near the threaded distal end 42.

Near this annular shoulder 48 there is also an upstanding ridge 50 formed on the fitment 38. This ridge 50 has a further increased outer diameter, compared to the rest of the fitment 38.

As can also be seen in FIG. 5, the interior cap wall surface 24 includes an interior threaded portion 52. This threaded portion 52 mates with the threaded distal end 42 of the luer fitment 38. The inner diameter of the threaded portion 52 is generally equal to the outer diameter of the threaded distal end 42 of the fitment 38.

An annular lip 54 extends outwardly from the exterior cap wall surface 22 at the open end 30 of the cap 14. As shown in FIG. 5, the lip 54 contacts the interior of the skirt 46, there forming a first sealed area 56.

Figure 6:
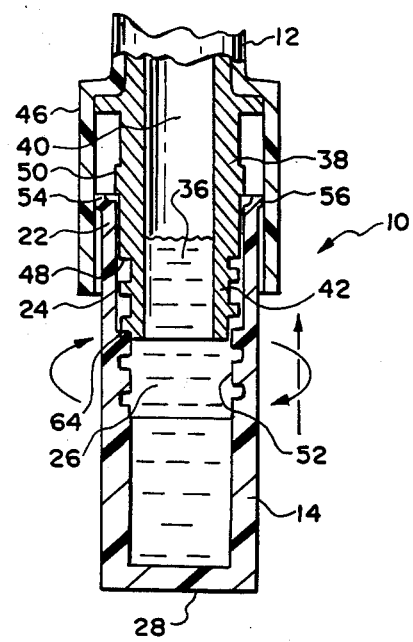
Figure 7:
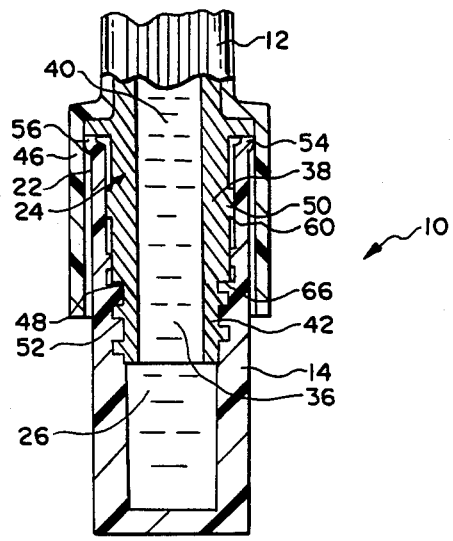

As can be seen in FIGS. 6 and 7, as the luer fitment 38 is progressively advanced into the interior chamber 26 of the cap 14, the first sealed area 56 formed between the annular lip 54 and the interior of the skirt 46 is continuously maintained.

As shown in FIG. 5, the region 58 of the cap 14 between its threaded portion 52 and its open end 30 has a larger inner diameter than the inner diameter of the threaded portion 52. This larger inner diameter is generally equal to the outer diameter of the ridge 50 formed on the fitment 38. Thus, as the luer fitment is progressively advanced into the interior chamber 26, a second sealed area 60 is formed between this cap region 58 and the ridge 50.

Also, as can be seen in FIGS. 6 and 7, as the fitment 38 is progressively advanced into the cap chamber 26, this second sealed area 60, like the heretofore described first sealed area 56, is continuously maintained.

By continously maintaining the first and second sealed areas 56 and 60 as the luer fitment 38 is progressively threaded onto the cap 14, leakage of the liquid antiseptic 36 from the cap chamber 26 is prevented.

Since leakage is prevented, the antiseptic is effectively trapped within the cap chamber 26. Thus, as the threaded distal end 42 of the fitment is progressively advanced, the incompressible liquid antiseptic 36 trapped in the cap chamber 26 is directed out of the cavity 26 and into the bore 40 of the fitment 38. This is shown in FIGS. 6 and 7.

When the cap 14 is fully threaded upon the connector 12 (see FIG. 7), the liquid antiseptic 36 occupies substantially all of the bore 40 of the fitment 38 and the adjacent portion of the extension set on catheter 16. As shown in FIG. 1, a clamp 62 is used to prevent the undesired transport of either the peritoneal dialysis solution out of the peritoneal cavity or the antiseptic 36 into the peritoneal cavity.

Because the inner diameter of the cap 14 in the region 88 is larger than the inner diameter in the threaded portion 52, an internal shoulder 64 is formed within the cap chamber 26. As shown in FIG. 7, when the cap 14 is fully threaded upon the luer fitment 38, the fitment shoulder 48 seats against the cap shoulder 64.

Together, the first and second sealed areas 56 and 60 effectively trap the antiseptic 36 within the confines of the cap chamber 26 as the fitment 38 is advanced to occupy more and more of the chamber 26. As a result, the antiseptic 36 has no place to escape other than into the bore 40 of the fitment 38.

Thereafter, when the cap 14 is completely attached to the connector 12, the first and second sealed areas 56 and 60 prevent leakage of the antiseptic 36 from the closure system 10 during use. Upon separation of the cap 14 from the connector 12, the skirt 46 serves to collect drops of antiseptic which may escape as the double seal arrangement is broken during separation, thereby preventing contact between the antiseptic and the user.

While, in the illustrated embodiment, the connector and the cap 14 are threaded together, the invention is operative in other configurations. For example, the luer fitment 38 can take the form of a spike member, and the cap 14 can be placed onto and off of the spike with a push-pull motion. As in the illustrated embodiment, by providing two seal areas between the spike and cap, the antiseptic can be trapped within the cap chamber 26 as the spike is inserted therein. The antiseptic will be directed onto the lumen of the spike as the spike and cap are joined, just as the antiseptic is directed into the bore 40 of the fitment 38 in the illustrated configuration.

An alternate embodiment of the cap 14 is shown in phantom lines in FIG. 5. There, the cap 14 includes a frangible membrane 68 which seals the antiseptic 36 within the cap chamber 26.

In this arrangement, because the antiseptic 36 is sealed within the cap chamber 26 by the membrane 68, a separate plug 36 need not be used.

As the threaded distal end 42 of the fitment 38 is advanced into the chamber 26, the frangible membrane 68 is broken by the fitment end 42. The liquid antiseptic 36 is then directed into the bore 40 of the fitment 38 in the manner heretofore described.

The components of the closure system 10 can be made of various materials, depending upon the operative environment in which they are used. In the context of peritoneal dialysis, the cap 14 is made of a suitable thermoplastic material which is capable of being sterilized and which is inert to the liquid antiseptic used. Antiseptics which may be used include sodium chloride and povidone iodine. The luer fitment 38 of the connector 12 can likewise be made of a sterilizable and inert thermoplastic material. Alternately a sterilizable and inert metallic material may be used, such as titanium or stainless steel. Preferably, the remainder of the connector 12 is made of a sterilizable and inert thermoplastic material.

Various features of the invention are set forth in the following claims.

We claim:

1. A closure system comprising
a connector including means for defining a luer fitment having an interior bore and wall means for defining a skirt peripherally surrounding said luer fitment,
a cap for joining to said connector, said cap having an exterior wall surface and an interior wall surface defining an interior chamber into which said luer fitment is advanced as said cap and connector are joined and in which a liquid antiseptic is retained, and
means associated with said cap and said connector forming a continuous first seal area between said exterior cap wall surface and said connector skirt and a continuous second seal area between said interior cap wall surface and said luer fitment for trapping the retained liquid antiseptic within said cap chamber as said cap and said connector are joined and for directing the liquid antiseptic from said cap chamber into said interior bore of said luer fitment as said luer fitment is advanced into said interior cap chamber.

2. A closure system according to claim 1
wherein said luer fitment includes an external threaded portion, and
wherein said interior cap wall includes a threaded portion which threadably engages said threaded portion of said luer fitment as said luer fitment is advanced into said interior cap chamber.

3. A closure system according to claim 1
wherein said means for forming said first seal area includes a lip formed on said exterior cap wall surface which sealingly contacts said connector skirt, the sealing contact being continuously maintained as said luer fitment is advanced into said interior cap chamber.

4. A closure system according to claim 1
wherein said means for forming said second seal area includes a ridge formed on said luer fitment which sealingly contacts said interior cap wall surface, the sealing contact being continuously maintained as said luer fitment is advanced into said interior cap chamber.

5. A closure system according to claim 1
wherein said cap includes a removable plug member for sealing said interior cap chamber prior to use.

6. A closure system according to claim 1
wherein said cap includes membrane means disposed within said interior cap chamber for normally sealing said interior cap chamber, and
wherein said luer fitment breaks said membrane to open said interior cap chamber as said luer fitment is advanced into said interior cap chamber.

* * * * *